United States Patent [19]
Junge et al.

[11] Patent Number: 6,001,857
[45] Date of Patent: Dec. 14, 1999

[54] HETEROCYCLYE SUBSTITUTED DIHYDROPYRIDINES

[75] Inventors: Bodo Junge; Wolfgang Hartwig; Heinrich Meier; Rudolf Schohe-Loop, all of Wuppertal, Germany; Zhan Gao, Beijing, China; Bernard Schmidt, Lindlar, Germany; Maarten de Jonge, Overath, Germany; Teunis Schuurman, Lohmar, Germany

[73] Assignee: Bayer Aktiengesellschaft, Leverkusen, Germany

[21] Appl. No.: 08/903,508

[22] Filed: Jul. 30, 1997

Related U.S. Application Data

[62] Division of application No. 08/572,770, Dec. 15, 1995, abandoned, which is a division of application No. 08/141,846, Oct. 22, 1993, Pat. No. 5,502,064.

[30] Foreign Application Priority Data

Oct. 30, 1992 [DE] Germany ............................. 42 36 707

[51] Int. Cl.$^6$ ................................................... A61K 31/44
[52] U.S. Cl. ........................................................ 514/336
[58] Field of Search ......................... 546/280.4; 514/336

[56] References Cited

U.S. PATENT DOCUMENTS

| | | | |
|---|---|---|---|
| 3,488,359 | 1/1970 | Bossert et al. | 546/321 |
| 3,574,843 | 4/1971 | Bossert et al. | 546/321 |
| 4,021,434 | 5/1977 | Murakami et al. | 546/321 |
| 4,406,906 | 9/1983 | Meyer et al. | 546/257 |
| 4,510,310 | 4/1985 | Wehinger et al. | 514/332 |
| 4,568,681 | 2/1986 | Wehinger et al. | 546/321 |
| 4,622,332 | 11/1986 | Wehinger et al. | 546/321 |
| 4,672,068 | 6/1987 | Kutsuma et al. | 514/336 |
| 4,727,066 | 2/1988 | Sunkel et al. | 514/161 |
| 4,849,433 | 7/1989 | Wehinger et al. | 546/321 |
| 4,988,717 | 1/1991 | Wehinger et al. | 546/321 |

FOREIGN PATENT DOCUMENTS

| | | |
|---|---|---|
| 026317 | 8/1980 | European Pat. Off. . |
| 088276 | 2/1983 | European Pat. Off. . |
| 239186 | 1/1987 | European Pat. Off. . |
| 1670824 | 4/1971 | Germany . |
| 2117571 | 4/1971 | Germany . |
| 2635916 | 2/1977 | Germany . |
| 2847236 | 5/1980 | Germany . |
| 3445356 | 6/1985 | Germany . |
| 3816361 | 12/1988 | Germany . |
| 1129158 | 11/1966 | United Kingdom . |

OTHER PUBLICATIONS

CA 103:178176, Kuehnis et al, 1985.
CA 109:190251x, Bky–Gulden, 1988.
Principles of Psychopharmacology, Clark et al. Academic Press, pp. 166–167, 1970.
Current Neurology vol. 6 Appel, pp. 289, 314–315, Year Book Medical Publishers, Inc., 1987.
Dihydropyridines—Progress in Pharmacology and Therapy (W.D. Bruse B. Garthoff F. Seuter (Eds.) 1993.
Diagnosis and Treatment of Senile Dementia (M. Bergener B. Reisberg (eds.) 1993.
Some Behavioral Effects of Repeated Administration of Calcium Channel Antagonists (Pharmacology Biochemistry & Behavior, vol. 35, pp. 557–560).
The FASEB Journal, vol. 3. (May 19890—Scriabine et al.
J. Heterocyclic Chem., Bd 25, Nr. 1, 1988, Seiten 81–87 Directed Lithiation of 4–halopyridines.
Eur. J. Med. Chem.—Chim. Ther., Bd. 18, Nr. 2, 1983, pp. 155–161.
J. Heterocycles, vol. 107, 1987, pp. 723.
J. Heterocycles, vol. 108, 1988—108:55919k—Chemical Abstract.
J. Heterocycles, vol. 111, 1989—111:2355u—Chemical Abstract.
Heterocycles, vol. 83, 1975,—28058n—Chemical Abstract.
Rampe, et al "Comparative aspects and temperature dependence of . . . " Sep. 8, 1986, pp. 1452–1460.
Derwent Abstract JP–239353 Aug. 30, 1988.
Trends Pharmacol. Sci. Bd. 11, Nr. 8, 1990, pp. 309–310, "Nimodipine and the recovery of memory".
Patent Abstracts of Japan, vol. 015, No. 425, (C–0879)29. Oct. 1991, & JP–A–31 76 471 (Sawai Seiyaku KK) Dec. 5., 1989.
Cupka et al., CA 108:5844M, 1988.
Vanden et al., CA 116:151512h, 1992.
Eynde et al., CA 116:194103t, 1992.
Yoshinaga, et al., CA 115:256001y, 1991.
Kusuma et al., CA 104:207168x, 1986.

*Primary Examiner*—Jane Fan
*Attorney, Agent, or Firm*—Sprung Kramer Schaefer & Briscoe

[57] ABSTRACT

4-Heterocyclyl-substituted dihydropyridines are prepared by reacting appropriate aldehydes with β-keto esters and aminocrotonic acid esters, or by esterifying 4-heterocyclyl-substituted dihydropyridinecarboxylic acids. The 4-heterocyclyl-substituted dihydropyridines can be employed in medicaments, in particular for the treatment of disorders of the central nervous system.

2 Claims, No Drawings

HETEROCYCLYE SUBSTITUTED DIHYDROPYRIDINES

This is a division of application Ser. No. 08/572,770, filed on Dec. 15, 1995 (now abandoned), which is a division of application Ser. No. 08/141,846, filed on Oct. 22, 1993 (now U.S. Pat. No. 5,502,064.

The present invention relates to 4-heterocyclyl-substituted dihydropyridines, processes for their preparation and their use in medicaments, in particular as agents for the treatment of disorders of the central nervous system.

The compound nimodipine and its cerebral activity have been disclosed [cf. German Offenlegungsschrift 2,815,578]. 4-Heterocyclyl-substituted dihydropyridines having a hypotensive action have additionally been disclosed [cf. JP 239,353; DE 3,816,361-A; EP 88,276 A; DE 3,239,273-A; DE 2,935,451; WO 84/02,132-A; U.S. Pat. No. 3,488,359; U.S. Pat. No. 3,574,843].

The present invention now relates to 4-heterocyclyl-substituted dihydropyridines of the general formula (I)

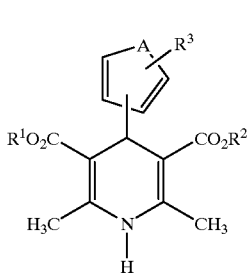

(I)

in which
R$^1$ and R$^2$ are identical or different and represent cycloalkyl having 3 to 8 carbon atoms, or represent straight-chain or branched alkyl having up to 8 carbon atoms, which is optionally substituted by straight-chain or branched alkoxy having up to 6 carbon atoms, cyano, cycloalkyl having 3 to 8 carbon atoms or aryloxy having 6 to 10 carbon atoms, which can be substituted, for its part, up to 3 times by identical or different halogen or cyano substituents or by straight-chain or branched alkyl or alkoxy having up to 6 carbon atoms, A represents a sulphur atom or the —C=N— group, and
R$^3$ represents hydrogen, halogen, trifluoromethyl or cyano,
and their salts.

Physiologically acceptable salts of the compounds according to the invention are preferred.

Physiologically acceptable salts are in general salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

The compounds according to the invention exist in stereoisomeric forms which either behave as image and mirror-image (enantiomers), or which do not behave as image and mirror-image (diastereomers). The invention relates both to the antipodes and to the racemic forms as well as the diastereomer mixtures. Like the diastereomers, the racemic forms can also be separated in a known manner into the stereoisomerically uniform constituents (cf. E. L. Eliel, Stereochemistry of Carbon Compounds, McGraw Hill, 1962).

Preferred compounds of the general formula (I) are those in which
R$^1$ and R$^2$ are identical or different and represent cyclopropyl, cyclopentyl, cyclohexyl or cycloheptyl, or represent straight-chain or branched alkyl having up to 6 carbon atoms, which is optionally substituted by straight-chain or branched alkoxy having up to 4 carbon atoms, cyano, cyclopropyl, cyclopentyl, cyclohexyl, cycloheptyl or phenoxy, which can be substituted, for its part, up to 3 times by identical or different fluorine or cyano substituents or by straight-chain or branched alkyl or alkoxy each having up to 4 carbon atoms, A represents a sulphur atom or the —C=N— group, and
R$^3$ represents hydrogen, fluorine, chlorine, bromine, trifluoromethyl or cyano,
and their salts.

Particularly preferred compounds of the general formula (I) are those
in which
R$^1$ and R$^2$ are identical or different and represent cyclopentyl, cyclohexyl or cycloheptyl, or represent straight-chain or branched alkyl having up to 4 carbon atoms, which is optionally substituted by methoxy, cyano, cyclopentyl, cyclohexyl or cycloheptyl, A represents a sulphur atom or the —C=N— group, and
R$^3$ represents hydrogen, chlorine, trifluoromethyl or cyano,
and their salts.

The following are very particularly preferred:
isopropyl 2-methoxyethyl 4-(2-chlorothien-3-yl)-1,4-dihydro-2,6-dimethylpyridine-3,5-dicarboxylate
cyclopentyl 2-methoxyethyl 4-(2-chlorothien-3-yl)-1,4-dihydro-2,6-dimethylpyridine-3,5-dicarboxylate
cyclopentyl 2-methoxyethyl 1,4-dihydro-2,6-dimethyl-4-(thien-3-yl)-pyridine-3,5-dicarboxylate
isopropyl 2-methoxyethyl 1,4-dihydro-2,6-dimethyl-4-(thien-3-yl)-pyridine-3,5-dicarboxylate
isopropyl 2-methoxyethyl 1,4-dihydro-2,6-dimethyl-4-(thien-3-yl)-pyridine-3,5-dicarboxylate
cyclopentyl 2-methoxyethyl 1,4-dihydro-2,6-dimethyl-4-(thien-2-yl)-pyridine-3,5-dicarboxylate
cyclopentyl 2-methoxyethyl 4-(4-cyano-pyridin-2-yl)-1,4-dihydro-2,6-dimethyl-pyridine-3,5-dicarboxylate
cyclopentyl 2-methoxyethyl 4-(6-cyano-pyridin-2-yl)-1,4-dihydro-2,6-dimethyl-pyridine-3,5-dicarboxylate
cyclohexylmethyl 2-methoxyethyl 1,4-dihydro-2,6-dimethyl-4-(pyridin-3-yl)-pyridine-3,5-dicarboxylate
cyclohexyl 2-methoxyethyl 1,4-dihydro-2,6-dimethyl-4-(pyridin-3-yl)-pyridine-3,5-dicarboxylate
cycloheptyl 2-methoxyethyl 1,4-dihydro-2,6-dimethyl-4-(pyridin-3-yl)-pyridine-3,5-dicarboxylate
cyclopentyl 2-methoxyethyl 1,4-dihydro-2,6-dimethyl-4-(pyridin-3-yl)-pyridine-3,5-dicarboxylate
cyclopentyl 2-methoxyethyl 1,4-dihydro-2,6-dimethyl-4-(pyridin-2-yl)-pyridine-3,5-dicarboxylate
isopropyl 2-methoxyethyl (+)-4-(2-chlorothien-3-yl)-1,4-dihydro-2,6-dimethyl-pyridine-3,6-dicarboxylate
isopropyl 2-methoxyethyl (−)-4-(2-chlorothien-3-yl)-1,4-dihydro-2,6-dimethyl-pyridine-3,6-dicarboxylate Processes for the preparation of the compounds of the general formula (I) according to the invention have additionally been found, characterised in that

[A] aldehydes of the general formula (II)

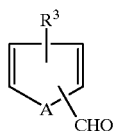

(II)

in which
R³ and A have the abovementioned meaning,
are first reacted with acetoacetic acid esters of the general formula (III)

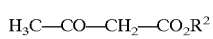

(III)

in which
R² has the abovementioned meaning,
if appropriate with isolation of the benzylidene compound, and the products are then reacted with 3-aminocrotonic acid esters of the general formula (IV)

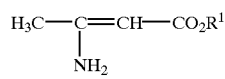

(IV)

in which
R¹ has the abovementioned meaning in inert solvents in the presence of a base and, if appropriate, acids, or

[B] compounds of the general formula (V)

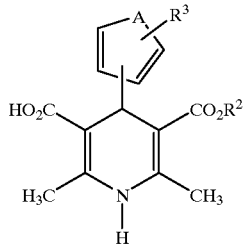

(V)

in which
R³ and R² have the abovementioned meaning, are reacted with the appropriate alcohols, if appropriate via a reactive acid derivative, in the presence of a base, where, by use of the enantiomerically pure derivatives of the compounds of the general formula (V), the corresponding enantiomers of the general formula (I) are obtained.

The processes according to the invention can be illustrated by way of example by the following reaction scheme:

[A]

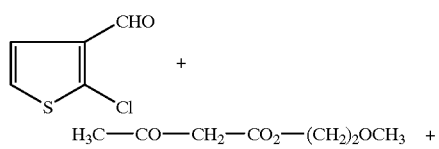

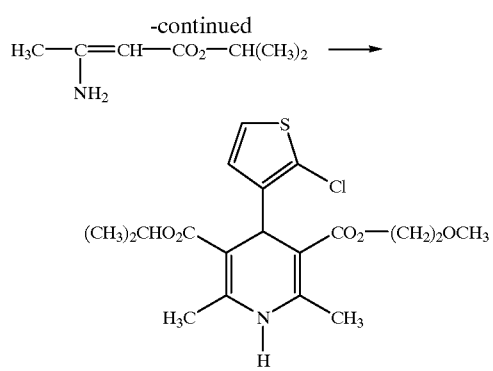

[B]

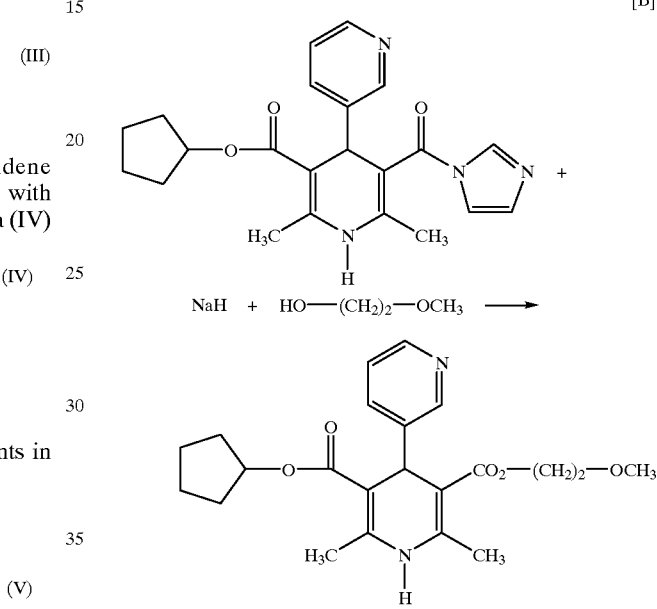

Suitable solvents for process [A] in this connection are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide, or dimethylformamide, or acetic acid or halogenated hydrocarbons such as methylene chloride, carbon tetrachloride or hydrocarbons such as benzene or toluene. It is also possible to use mixtures of the solvents mentioned. Isopropanol, ethanol, tetrahydrofuran, methanol, dioxane and dimethylformamide are preferred.

Suitable solvents for process [B] are the abovementioned solvents with the exception of the alcohols.

Suitable bases are in general alkali metal hydrides or alkoxides, such as, for example, sodium hydride or potassium tert-butoxide, or cyclic amines, such as, for example, piperidine, dimethylaminopyridine or $C_1$—$C_4$-alkylamines, such as, for example, triethylamine. Depending on the particular reaction steps, those preferred are piperidine, dimethylaminopyridine, pyridine, sodium hydride and potassium tert-butoxide.

In the case of process [A], suitable acids are organic $C_1$—$C_3$-carboxylic acids, such as, for example, acetic acid or propionic acid. Acetic acid is preferred.

When carrying out the processes according to the invention, any desired ratio of the substances participating in the reaction can be used. In general, however, molar amounts of the reactants are used.

The reaction temperatures can be varied within a relatively wide range. In general, the reaction is carried out between +10° C. and +150° C., preferably between +20° C. and +100° C., in particular at the boiling point of the respective solvent.

The reactions can be carried out at normal pressure, but also at elevated or reduced pressure (for example 0.5 to 3 bar). In general, the reactions are carried out at normal pressure.

Some reaction steps are carried out under a protective gas atmosphere.

To activate the carboxylic acid, suitable reagents are the customary reagents such as inorganic halides, for example thionyl chloride, phosphorus trichloride or phosphorus pentachloride, or carbonyldiimidazole, carbodiimides such as cyclohexylcarbodiimide or 1-cyclohexyl-3-[2-(N-methylmorpholino)ethyl]-carbodiimide-p-toluenesulphonate or N-hydroxyphthalimide or N-hydroxybenzotriazole.

Enantiomerically pure forms are obtained, for example, by separating diastereomer mixtures of the compounds of the general formula (I) in which $R^2$ or $R^3$ represents an optically active ester radical by a customary method, then either directly transesterifying or first preparing the chiral carboxylic acids and then preparing the enantiomerically pure dihydropyridines by esterification.

Ester radicals suitable as chiral ester radicals are all esters of enantiomerically pure alcohols such as, for example, phenylethanol, lactic acid, lactic acid esters, mandelic acid, mandelic acid esters, 2-aminoalcohols, sugar derivatives, hydroxyaminoacetic acid derivatives and many other enantiomerically pure alcohols.

In general, the diastereomers are either separated by fractional crystallisation, by column chromatography or by Craig partition. It must be decided from case to case which is the optimal process; sometimes it is also expedient to use combinations of the individual processes. Separation by crystallisation or Craig partition or a combination of both processes is particularly suitable.

The enantiomerically pure compounds are also accessible by chromatography of the racemic esters on chiral phases.

The compounds of the general formula (II) are known per se or can be prepared by known processes.

The acetoacetic acid derivatives of the general formula (III) are known or can be prepared by known processes.

The aminocrotonic acid derivatives of the formula (IV) are known or can be prepared by known processes.

The compounds of the general formula (V) are new and can be prepared by first treating compounds of the general formula (II) with acetoacetic esters of the general formula (III) and then with compounds of the general formula (VI)

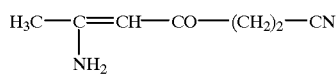

(VI)

as described under process [A], and treating the resulting dihydropyridine cyanoethyl ester with one of the abovementioned bases, preferably sodium hydroxide or potassium tert-butoxide.

The above preparation processes are only given for clarification. The preparation of the compounds of the general formula (I) is not restricted to these processes, but any modification of these processes is applicable in the same manner for the preparation of the compounds according to the invention.

The compounds according to the invention show an unforeseeable, useful spectrum of pharmacological activity.

The compounds according to the invention are calcium channel ligands with selectivity for L-type calcium channels of the central nervous system. This selectivity can be seen, for example, by comparison of the binding affinities to DHP binding sites in rats' brains and rats' hearts.

The compounds positively affect learning and memory powers, as their power-enhancing effect on rats in typical learning and memory models such as the water maze, Morris maze, passive avoidance and memory tests in automated Skinner boxes demonstrates. They have an antidepressive potential, as their activity in the rat swimming tests according to Porsolt confirms.

Binding Assays

The binding affinities to PN-200-110 binding sites in rats' brains or rats' hearts are determined according to Rampe D. R., Mutledge, Janis R. A., Triggle D. J.: Can. Journ. Physiol. Pharmacol. 65, (1987) 1452.

Water Maze

Old Wistar rats (24 months) are placed in the starting position in a plastic tank (120×50×40 cm) filled with cold (14–15°) water and subdivided by vertical barriers. In order to reach a ladder which enables the animals to escape from the water, they must swim around these barriers. The time which is required for finding the exit and the number of errors on the way there are recorded. In this case, an error is defined as swimming up a blind alley or swimming over the boundary of imaginary squares into which the tank is subdivided in the direction away from the exit.

The rats remain in the maze until finding the exit, but at longest 300 sec. They are then taken out, dried and warmed under a red light. They then return to their home cages.

In a typical experiment, two equivalent animal groups (placebo, test substance each n=15) are determined by means of a preliminary test. The animals then go through 6 test sessions, two per day. Test substances or placebo are administered orally 30 min before the experiments. The measure of the learning- and memory-enhancing effect of the test substances in comparison to placebo is reduction of the time until reaching the exit, reduction of the number of errors and increase in the number of animals which find the exit at all.

Rat Swimming Test According to Porsolt

During a preliminary test, young rats are placed in a glass cylinder (40 cm high, 20 cm diameter) which is filled 17 cm high with water at 25° C. After 20 min in the water, the animals are taken out and warmed under a lamp for 30 min. In this preliminary test, all rats attempt to get out of the cylinder until after about 15 min they remain immobile ("behavioural despair", giving-up behaviour). 24 h later, the test session starts in which the rats are placed in the glass cylinder as on the previous day, but this time for only 5 min. The lengths of time for which the rats remain immobile during this 5 min are recorded. In this case, a rat is regarded as immobile which, floating upright in the water, only carries out minimal movements in order to keep its head above water. Placebo or test substances (0.25, 0.5, 1, 5, 10 mg/kg; n=6 per group) are administered orally three times; 23, 5 and 1 h before the test session (1, 19, 23 h after the preliminary test). The antidepressive effect of the test substances is seen in the reduction of the period of immobility in comparison to the placebo values. As a result of their pharmacological properties, the compounds can be employed for the preparation of medicaments for the treatment of central degenerative disorders, as, for example, occur in dementias (multi-infarct dementia, MID, primary degenerative dementia PDD, pre- and senile Alzheimer's disease, HIV dementia and other forms of dementia), Parkinson's disease or amyotropic lateral sclerosis.

The active compounds are furthermore suitable for the treatment of cerebral function disorders in old age, of organic brain syndrome (OBS) and of age-associated memory impairment (AAMI).

They are useful for the prophylaxis and for the control of the sequelae of cerebral circulatory disorders such as cerebral ischaemias, strokes and of subarachnoid haemorrhages and for the treatment of brain traumas.

They are suitable for the treatment of depressions.

Further areas of application are the treatment of migraine, of neuropathies, of addictive disorders and withdrawal symptoms.

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the excipient(s) or auxiliary(-ies).

In general, it has proven advantageous to administer the active compound(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may sometimes be advantageous to deviate from the amounts mentioned, namely depending on the type and the body weight of the subject treated, on individual behaviour towards the medicament, the nature and severity of the disorder, the type of preparation and administration, and the time and interval at which administration takes place.

The $R_f$ values shown in each case were determined—if not stated otherwise—by thin layer chromatography on silica gel (aluminium foil, silica gel 60 F 254, E. Merck). The substance spots were visualised by observation under UV light and/or by spraying with 1% strength potassium permanganate solution.

Flash chromatography was carried out on silica gel 60, 0.040–0.064 mm, E. Merck. Elution with solvent gradients means: starting with the pure, non-polar solvent mixture component, the polar eluent component is admixed to an increasing extent until the desired product is eluted (TLC checking).

PREPARATION EXAMPLES

Example 1

3-(2-Methoxyethyl) 5-(2-cyanoethyl) 4-(2-chlorothien-3-yl)-1,4-dihydro-2,6-dimethyl-pyridinedicarboxylate

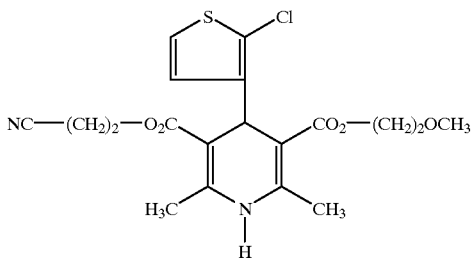

14.7 g (100 mmol) of 2-chlorothiophene-3-aldehyde, 16.0 g (100 mmol) of 2-methoxyethyl acetoacetate and 15.4 g (100 mmol) of 2-cyanoethyl 3-aminocrotonate are reacted in 150 ml of isopropanol. 23.1 g (54%) of the title compound of m.p. 112–114° C. are obtained, which is reacted further as a crude product.

Further Reaction 22.9 g (54 mmol) of the compound from Example 1 are dissolved in 229 ml of 1,2-dimethoxyethane. 72 ml of 1N sodium hydroxide solution are added dropwise at room temperature in the course of 30 min and the reaction solution is stirred at room temperature for 18 h. 72 ml of 1N hydrochloric acid are then added dropwise and, after this, a further 85 ml of water, whereupon slow crystallisation commences. The mixture is cooled to 15° C. for a further 2 h and the crystallisate is filtered off with suction. 9.6 g (48%) of 4-(2-chlorothien-3-yl)-1,4-dihydro-2,6-dimethyl-pyridine-3,5-dicarboxylic acid 2-methoxyethyl monoester of m.p. 157–159° C. (dec.) are obtained. A further 8.5 g of m.p. 150–157° C. are obtained from the mother liquor after concentration to half the volume.

Example 2

Isopropyl 2-methoxyethyl 4-(2-chlorothien-3-yl)-1,4-dihydro-2,6-dimethyl-pyridine-3,5-dicarboxylate

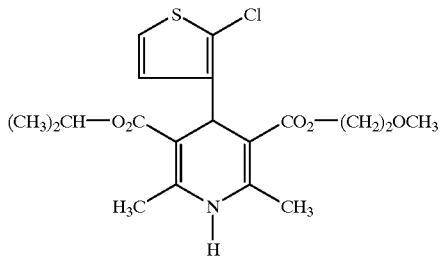

A) 7.3 g (50 mmol) of 2-chlorothiophene-3-aldehyde are dissolved in 75 ml of isopropanol with 7.2 g (50 mmol) of isopropyl acetoacetate. After addition of 0.35 ml (3.5 mmol) of piperidine and 0.20 ml (3.5 mmol) of acetic acid in 6 ml of isopropanol, the mixture is heated to 40° C. for 2 h, then 8.0 g (50 mmol) of 2-methoxyethyl 3-aminocrotonate are added and the mixture is stirred at 40° C. for a further 8 h. After cooling, the batch is stirred into a mixture of 400 ml of water and 200 ml of toluene. The aqueous phase is extracted once more with 100 ml of toluene and the combined organic phases are washed with 100 ml each of 0.1 N hydrochloric acid and 1% strength sodium hydrogencarbonate solution, twice with 100 ml each of water and dried over sodium sulphate. The crude product fractions obtained after concentration to about 75 ml, filtration, further concentration, precipitation with petroleum ether and fresh filtration are purified by chromatography on silica gel in ethyl acetate/cyclohexane 1:1 and crystallisation from ethyl acetate/cyclohexane. 8.5 g (41%) of the target compound of m.p. 125–126° C. are obtained. A further 2.7 g (13%) of the same melting point are obtained from the mother liquor.

B) 5.6 g (15 mmol) of 4-(2-chlorothiophen-3-yl)-1,4-dihydro-2,6-dimethyl-pyridine-3,5-dicarboxylic acid 2-methoxyethyl monoester are heated to 50° C. in 50 ml of anhydrous tetrahydrofuran. 2.7 g (16.5 mmol) of carbonyldiimidazole, dissolved in 35 ml of anhydrous tetrahydrofuran, are added and the mixture is stirred for about 1 h until the evolution of carbon dioxide is complete. 100 ml of solvent is then removed by distillation under normal pressure and 100 ml of isopropanol are added at the same time, as a result of which a boiling point of 82° C. is reached. The mixture is then kept at boiling for a further 24 h (thin layer chromatographic checking of the conversion in cyclohexane/ethyl acetate 30:70). For working-up, the mixture is added to a mixture of 400 ml of 5% strength sodium chloride solution, 33 ml of 1N hydrochloric acid and 200 ml of toluene and the aqueous phase is extracted once more with toluene after separation of the phases. The combined organic phases are washed with 100 ml each of 0.1 N hydrochloric acid, sodium hydrogencarbonate solution and twice with water, dried over sodium sulphate and concentrated to about 50 ml. The crude product precipitated after addition of 100 ml of petroleum ether is purified by chromatography on silica gel in cyclohexane/ethyl acetate 1:1 and crystallisation from cyclohexane/ethyl acetate. 3.9 g (63%) of the target compound of melting point 123–124° C. are thus obtained.

The compounds shown in Table 1 are prepared in analogy to the procedure of Example 2:

TABLE 1

| Ex. no. | R | $R^1$ | m.p. ° C./$R_f$* (enantiomer/racemate) | Preparation analogous to method |
|---|---|---|---|---|
| 3 | 2-chloro-3-thienyl | cyclopentyl | 117–118 | B |
| 4 | 3-thienyl | cyclopentyl | 112–113.5 | |
| 5 | 3-thienyl | —CH(CH$_3$)$_2$ | 95–96 | B |
| 6 | 2-methyl-3-thienyl | cyclopentyl | 94–95 | B |
| 7 | 2-thienyl | —CH(CH$_3$)$_2$ | 108–109 | B |

TABLE 1-continued

[Structure: dihydropyridine core with R at 4-position, R¹—O₂C— and —CO₂—(CH₂)₂—OCH₃ at 3,5-positions, H₃C and CH₃ at 2,6-positions, N–H]

| Ex. no. | R | R¹ | m.p. °C./R$_f$* (enantiomer/racemate) | Preparation analogous to method |
|---|---|---|---|---|
| 8 | 2-methyl-4-cyanopyridin-3-yl | cyclopentyl (methyl-substituted) | 176–177 | A |
| 9 | 6-methyl-2-cyanopyridin-3-yl | cyclopentyl (methyl-substituted) | 147–148 | A |
| 10 | pyridin-3-yl (methyl-substituted) | —H₂C-cyclohexyl | 178 | B |
| 11 | pyridin-3-yl (methyl-substituted) | cyclohexyl | 156–157 | B |
| 12 | pyridin-3-yl (methyl-substituted) | cycloheptyl | 147 | B |
| 13 | pyridin-2-yl (methyl-substituted) | cyclopentyl (methyl-substituted) | 151–152 | A |
| 14 | pyridin-3-yl (methyl-substituted) | cyclopentyl (methyl-substituted) | 166 | B |
| 15* | 2-chloro-3-methylthien-5-yl | —CH(CH₃)₂ | 0.48$^{a)}$ (+) (enantiomer (ee ≧ 98%; a$_D^{20}$ = +14.96*) | |

TABLE 1-continued

![Structure: R1-O2C and CO2-(CH2)2-OCH3 substituted 1,4-dihydro-2,6-dimethylpyridine with R at 4-position]

| Ex. no. | R | R¹ | m.p. °C./$R_f$* (enantiomer/racemate) | Preparation analogous to method |
|---------|---|----|--------------------------------------|-------------------------------|
| 16* | [2-chloro-3-methylthien-... structure] | —CH(CH₃)₂ | 0.48[a)] <br> (−) (enantiomer (ee ≧ 94.9%; $a_D^{20}$ = −13.31*) | |
| 17* | [cyanopyridine structure] | [cyclopentyl] | (−) (enantiomer (ee ≧ 98.15%; $a_D^{20}$ = −14.62*) | |
| 18* | [cyanopyridine structure] | [cyclopentyl] | (+) (enantiomer (ee ≧ 97.85%; $a_D^{20}$ = +11.41*) | |

*Obtained by separation on a chiral column
[a)] cyclohexane:Ethyl acetate 30:70

We claim:

1. A method of treating depression or senile dementia in a patient in need thereof which comprises administering to such patient an amount effective therefor of a compound or salt thereof selected from the group consisting of isopropyl 2-methoxyethyl 4-(2-chlorothien-3-yl)-1,4-dihydro-2,6-dimethylpyridine-3,5-dicarboxylate cyclopentyl 2-methoxyethyl 4-(2-chlorothien-3-yl)-1,4-dihydro-2,6-dimethylpyridine-3,5-dicarboxylate cyclopentyl 2-methoxyethyl 1,4-dihydro-2,6-dimethyl-4-(thien-3-yl)-pyridine-3,5-dicarboxylate isopropyl 2-methoxyethyl 1,4-dihydro-2,6-dimethyl-4-(thien-2-yl)-pyridine-3,5-dicarboxylate isopropyl 2-methoxyethyl 1,4-dihydro-2,6-dimethyl-4-(thien-3-yl)-pyridine-3,5-dicarboxylate cyclopentyl 2-methoxyethyl 1,4-dihydro-2,6-dimethyl-4-(thien-2-yl)-pyridine-3,5-dicarboxylate isopropyl 2-methoxyethyl (+)-4-(2-chlorothien-3-yl)-1,4-dihydro-2,6-dimethyl-pyridine-3,6-dicarboxylate isopropyl 2-methoxyethyl (−)-4-(2-chlorothien-3-yl)-1,4-dihydro-2, 6-dimethyl-pyridine-3,6-dicarboxylate.

2. A method of treating depression or senile dementia which comprises administering an effective amount of a compound of the formula

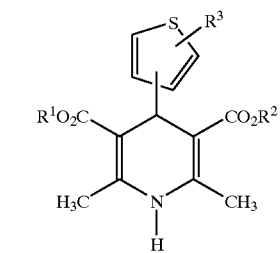

(I)

in which
  R¹ and R² are identical or different and represent cycloalkyl having 3 to 8 carbon atoms, or represent straight-chain or branched alkyl having up to 8 carbon atoms, which is optionally substituted by straight-chain or branched alkoxy having up to 6 carbon atoms, cyano, cycloalkyl having 3 to 8 carbon atoms or aryloxy having 6 to 10 carbon atoms, which can be substituted, for its part, up to 3 times by identical or different halogen or cyano substituents or by straight-chain or branched alkyl or alkoxy having up to 6 carbon atoms, and
  R³ represents hydrogen, trifluoromethyl or cyano
or a salt thereof,
to a patient in need thereof.

* * * * *